(12) United States Patent
Bukhman

(10) Patent No.: US 9,999,750 B2
(45) Date of Patent: Jun. 19, 2018

(54) METHOD AND SYSTEM OF UTILIZING ECG SIGNAL FOR CENTRAL VENOUS CATHETER TIP POSITIONING

(71) Applicant: C. R. Bard, Inc., Murray Hill, NJ (US)

(72) Inventor: Vladislav Bukhman, East Northport, NY (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days. days.

(21) Appl. No.: 15/286,418

(22) Filed: Oct. 5, 2016

(65) Prior Publication Data

US 2017/0021131 A1    Jan. 26, 2017

Related U.S. Application Data

(63) Continuation of application No. 14/772,069, filed as application No. PCT/US2014/019664 on Feb. 28, (Continued)

(51) Int. Cl.
*A61B 5/04* (2006.01)
*A61M 25/01* (2006.01)
(Continued)

(52) U.S. Cl.
CPC ............. *A61M 25/01* (2013.01); *A61B 5/042* (2013.01); *A61B 5/065* (2013.01); *A61B 5/6852* (2013.01);
(Continued)

(58) Field of Classification Search
CPC . A61B 2505/03; A61B 2505/05; A61B 34/20; A61B 5/042; A61B 5/065; A61B 5/6852; A61B 5/7221; A61M 2025/0166; A61M 2205/13; A61M 2205/18; A61M 2205/50; A61M 2210/125; A61M 2230/005; A61M 2230/04; A61M 25/01; G06F 17/18; Y02E 10/549

See application file for complete search history.

(56) References Cited

U.S. PATENT DOCUMENTS 7,289,844 B2    10/2007   Misczynski et al.
9,463,301 B2    10/2016   Bukhman
(Continued)

FOREIGN PATENT DOCUMENTS

CN    101939738 A    1/2011
GB    2 335 747 A    9/1999
(Continued)

OTHER PUBLICATIONS

EP 14760648.7 filed Aug. 31, 2015 Supplementary Search Report dated Sep. 2, 2016.
(Continued)

*Primary Examiner* — George Manuel
(74) *Attorney, Agent, or Firm* — Rutan & Tucker, LLP

(57) ABSTRACT

Disclosed herein are a method and a medical system for utilizing of an intravascular ECG signal for central venous catheter placement. The medical system is capable of detecting the position of a catheter tip and assessing its location relative to the cavoatrial junction. The detection and assessment are performed by a multiscale analysis of the complexity of the intravascular signal data points.

20 Claims, 8 Drawing Sheets

Related U.S. Application Data 2014, now Pat. No. 9,463,301, which is a continuation of application No. 13/844,755, filed on Mar. 15, 2013, now Pat. No. 9,220,432.

(60) Provisional application No. 61/771,825, filed on Mar. 2, 2013.

(51) Int. Cl.
*A61B 5/042* (2006.01)
*A61B 5/06* (2006.01)
*G06F 17/18* (2006.01)
*A61B 34/20* (2016.01)
*A61B 5/00* (2006.01)

(52) U.S. Cl.
CPC ............ *A61B 5/7221* (2013.01); *A61B 34/20* (2016.02); *G06F 17/18* (2013.01); *A61B 2505/03* (2013.01); *A61B 2505/05* (2013.01); *A61M 2025/0166* (2013.01); *A61M 2205/13* (2013.01); *A61M 2205/18* (2013.01); *A61M 2205/50* (2013.01); *A61M 2210/125* (2013.01); *A61M 2230/005* (2013.01); *A61M 2230/04* (2013.01); *Y02E 10/549* (2013.01)

(56) References Cited

U.S. PATENT DOCUMENTS

| | | | |
|---|---|---|---|
| 2008/0234978 A1 | 9/2008 | Neumann et al. | |
| 2009/0005675 A1* | 1/2009 | Grunwald | A61B 5/7405 600/424 |
| 2009/0259124 A1 | 10/2009 | Rothenberg | |
| 2010/0261977 A1 | 10/2010 | Seely | |
| 2010/0317981 A1 | 12/2010 | Grunwald | |
| 2013/0150740 A1 | 6/2013 | Narayan et al. | |
| 2014/0249505 A1 | 9/2014 | Bukhman | |

FOREIGN PATENT DOCUMENTS

| | | |
|---|---|---|
| WO | 2009043144 A1 | 4/2009 |
| WO | 2010/125116 A1 | 11/2010 |
| WO | 2012/040487 A1 | 3/2012 |
| WO | 2014137841 A1 | 9/2014 |

OTHER PUBLICATIONS

PCT/US2014/019664 filed Feb. 28, 2014 International Search Report and Written Opinion dated May 30, 2014.

Pittiruti, et al. "The EKG Method for Positioning the Tip of PICCs: Results from Two Preliminary Studies." JAVA, vol. 13, No. 4, pp. 179-185, 2008.

U.S. Appl. No. 13/844,755, filed Mar. 15, 2013 Non-Final Office Action dated Feb. 25, 2015.

U.S. Appl. No. 13/844,755, filed Mar. 15, 2013 Notice of Allowance dated Aug. 28, 2015.

U.S. Appl. No. 14/772,069, filed Sep. 1, 2015 Non-Final Office Action dated Apr. 27, 2016.

CN 201480011618.6 filed Aug. 31, 2015 Office Action dated Jun. 27, 2017.

* cited by examiner

METHOD AND SYSTEM OF UTILIZING ECG SIGNAL FOR CENTRAL VENOUS CATHETER TIP POSITIONING

PRIORITY

This application is a continuation of U.S. patent application Ser. No. 14/772,069, filed Sep. 1, 2015, now U.S. Pat. No. 9,463,301, which is a U.S. national stage application under 35 USC § 371 of International Application No. PCT/US2014/019664, filed Feb. 28, 2014, which claims the benefit of priority to U.S. patent application Ser. No. 13/844,755, filed Mar. 15, 2013, now U.S. Pat. No. 9,220,432, which claims the benefit of priority to U.S. Provisional Application No. 61/771,825, filed Mar. 2, 2013, each of which is incorporated by reference in its entirety into this application.

BACKGROUND

Various endovascular devices, including without limit central venous catheters ("CVC"), may be inserted into the vasculature of a patient to detect and/or treat various health issues. CVCs are endovascular devices including any catheter designed to utilize the central veins (e.g., subclavian and superior vena cava) or right sided cardiac chambers for the delivery and/or withdrawal of blood, blood products, therapeutic agents, and/or diagnostic agents. CVCs also include catheters inserted into the central veins or right sided cardiac chambers for the acquisition of hemodynamic data. Standard central venous catheters for intravenous access, dialysis catheters, percutaneously introduced central catheters ("PICC" lines), and right heart ("Swan-Ganz™") catheters are examples of CVCs. In some applications, an endovascular device, e.g., a central venous catheter (CVC), may be inserted into the superior vena cava (SVC) of a patient.

The specific location placement of an endovascular device is very important and can have a significant impact on the health of the patient. For example, a central venous catheter (CVC) with its tip located in the ideal position provides reliable vascular access with optimal therapeutic delivery, while minimizing short and long-term complications. In the United States, the ideal catheter tip placement of a CVC in the SVC is within 10 mm from the junction of the SVC and the right atrium (i.e., the "cavoatrial junction"). According to FDA, the tip of catheter should not be placed in, or allowed to enter, the right atrium of the heart. In 1989, the Food and Drug Administration issued a warning citing an increased risk of perforation of the right atrium, clot formation, and arrhythmias among other potential complications resulting from the tip of the CVC being placed inside the right atrium.

While CVCs have been used for many years, determining the position of the tip of the CVC has always been problematic. Further, in addition to the need to know where the tip is during initial placement, the CVC may migrate or otherwise move after the initial placement and require re-positioning. Therefore, the operator must monitor or periodically reevaluate the location of the tip.

Electrocardiogram (ECG) based guidance can be used as a positioning technique for catheter tip placement and confirmation. The electrical conduction system of the heart creates specific electrical signals, electrical energy distributions and behaviors thereof which are indicative of specific locations in the thoracic cavity and/or of specific heart functions or conditions. When measured endovascularly or intravascularly, i.e., from within blood vessels or from within the heart, certain parameters of the electrical activity of the heart can be used to identify specific locations in the cardiovascular system and/or functional conditions, normal or abnormal. An electrocardiogram (ECG) measures electrical potential changes occurring in the heart. The P wave portion of the ECG waveforms represents atrial muscle depolarization: the first half is attributable to the right atrium and the second half to the left atrium. Under normal circumstances, atrial muscle depolarization is initiated by a release of an excitatory signal from the sino-atrial node, a specialized strip of tissue located at the juncture of the superior vena cava ("SVC") and right atrium.

Some methods of ECG based guidance employ morphological and/or spectral analysis of ECG waveforms, specifically P waves, to position a catheter tip. (See Patent Application Publication US2010/0317981, which is incorporated by reference in its entirety into this application). Techniques of using ECG waveforms to locate the tip of a CVC have shown that both the magnitude and shape of the P wave changes depending upon the positioning or location of the electrode attached to the tip of the CVC. Normally as the electrode attached to the tip of the CVC moves from the SVC toward the sino-atrial node, the maximum value of the absolute value of the voltage of the P wave increases.

However, placement or location methods using P wave or other ECG waveform analysis have many disadvantages. For example, it is difficult to detect the exact location of the tip within last one-third of the SVC before the cavoatrial junction using this method. Accordingly, the final fixed position of the tip is not always optimal. Further, to identify the proper tip position, one must identify the point where the P wave is tallest; however, to identify the tallest P wave clinicians generally must "cross-the-line" by briefly entering the atrium (i.e., they must move beyond the point where the P wave is tallest to know where the tallest point is). This entry into the atrium is contrary to FDA regulations and causes additional and unnecessary risks for the patient. Also, successful placement of the CVC using this method ends up depending a great deal on the experience of the clinician, and is more difficult for less experienced clinicians. Another disadvantage of methods focused on analyzing P waves or other waveforms is that heart abnormalities, arrhythmias, anatomic variability, noise and artifacts may affect detection and interpretation of P-waves morphological changes.

Disclosed herein are new methods of objective assessment of the location of the catheter tip by analyzing ECG data point to point variability, which avoids the above disadvantages. The method evaluates the complexity of changes of an ECG signal to calculate the distance from the catheter tip to the cavoatrial junction. The method is based on chaos theory and the concept of self-organized criticality (SOC). Systems at critical transition point between chaos and order are said to be in a state of self-organized criticality. The concept of SOC may be applied in different areas such as biological systems, statistics, nature, and large electronic circuits.

SUMMARY OF THE INVENTION

Described herein are new methods and systems for endovascular device placement, and new methods and systems for assessing of the location of an endovascular device. In one embodiment, the method and system involves utilizing electrocardiogram (ECG) signal for positioning the tip of a device, e.g. a CVC, in vasculature.

In one embodiment, the method includes receiving time series data relating to intravascular ECG (ivECG) of the patient from a CVC placement device; measuring Proximity Index (PxI) using multiscale complexity analysis of ivECG time series of the patient; comparing the determined PxI with proximity thresholds related to distances from the CVC tip to cavoatrial junction; and providing an output indicative of position of the CVC tip in the SVC relative to the cavoatrial junction.

In one embodiment, a method of utilizing an ECG signal for positioning a tip of a central venous catheter (CVC) includes receiving ivECG signal data, determining at least one PxI parameter, wherein the PxI parameter is a chaos theory complexity parameter associated with variability of the ivECG signal data. The method may also include comparing the at least one PxI parameter with a proximity threshold of a tip of the CVC to the cavoatrial junction, and providing an output indicative of proximity of the CVC tip to the cavoatrial junction.

In one embodiment, a method of positioning an endovascular device in vasculature, includes advancing an endovascular device into the vasculature, the endovascular device having an electrode for receiving ivECG signal data, receiving ivECG signal data using the electrode, and determining at least one PxI parameter based on the received ivECG signal data. The method may also include comparing the at least one PxI parameter with a proximity threshold indicating a location of the endovascular device in relation to a part of a patient's body, and providing an output indicative of proximity of the endovascular device to the part of the patient's body.

In one embodiment a medical system for CVC placement comprises a CVC placement unit and ivECG processing unit. The CVC placement unit provides tools and means for placing CVC through one of central vein and comprises of the CVC placement device and ivECG acquisition module. The ivECG processing unit receives the ivECG signal from the CVC placement unit, calculates PxI values, compares those values with proximity to cavoatrial junction thresholds and provides this info to audio and/or visualization module.

BRIEF DESCRIPTION OF THE DRAWINGS

The invention may be understood by reference to the following description taken in conjunction with the accompanying drawings, in which like reference numerals identify like elements, and in which.

Figure 1:
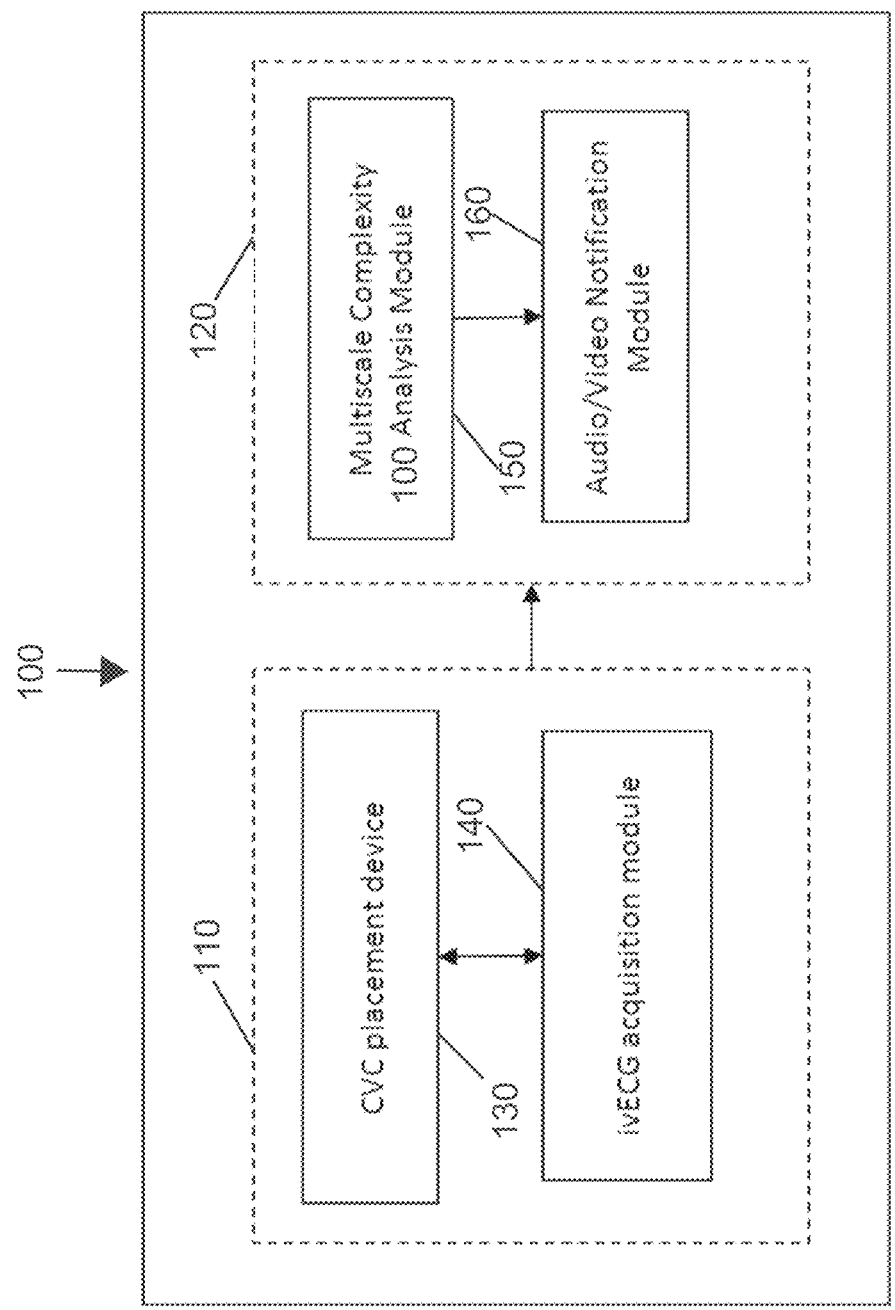
FIG. 1 shows a stylized diagram of a medical system that includes a CVC placement unit and a signal processing unit, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Described herein are methods and systems for endovascular device placement and assessing endovascular device location including features/steps believed to provide advantages over existing placement and location assessment methods and systems. Illustrative embodiments are described herein.

General methods and systems are described herein sufficient to enable one to develop a variety of implementations/applications without undue experimentation. In the development of particular applications, numerous implementation-specific decisions will be made to achieve the design-specific goals, which will vary from one implementation/application to another. It will be appreciated that such a development effort would be a routine undertaking for persons of ordinary skill in the art having the benefit of this disclosure.

This document does not intend to distinguish between components that differ in name but not function. In the following discussion and in the claims, the terms "including," "includes," "comprising," "have," and "has" are used in an open-ended fashion, and thus should be interpreted to mean "including, but not limited to." The word "or" is used in the inclusive sense (i.e., "and/or") unless a specific use to the contrary is explicitly stated.

In one embodiment, discussed in detail below, the present invention provides a system and method for positioning of a CVC tip in the SVC. While this system and method may be discussed in terms of placing a CVC tip in the SVC, the principles used in the system and method may be applied to a broader range of systems, methods, and devices. For example, the principles may be applied to implanting different types of catheters or devices (e.g., CVC, PICC, pacemaker leads, guiding guidewires) in the SVC or in selected veins, arteries, or parts of the body other than, or in addition to, the SVC to achieve particular results.

As discussed in more detail below, the system and method evaluate the complexity of changes of an ivECG signal to calculate the position of an endovascular device, e.g., to calculate the distance from the tip of a CVC to the cavoatrial junction. The method is based on chaos theory and the concept of self-organized criticality (SOC).

FIG. 1 shows a simplified block diagram of an endovascular placement system in the form of a CVC placement system 100. CVC placement system 100 includes CVC placement unit 110 and signal processing unit 120. CVC placement unit 110 includes CVC placement device 130 and ivECG signal acquisition module 140. CVC placement unit 110 can be any type of endovascular device placement/confirmation system, e.g., any vein or artery catheterization or tip placement/confirmation system. For example, CVC placement unit 110 may be the Sherlock 3CG® Tip Confirmation System by Bard Access Systems, or a similar endovascular device placement system. The CVC placement unit 110 may include a variety of hardware and software used for inserting an endovascular device and sensing/acquiring signals related to device placement/confirmation. The CVC placement device 130 may include any components necessary to place the endovascular device. The iVECG signal acquisition module 140 may be a combination of hardware and software used to acquire a signal, e.g., an iVECG signal.

The signal processing unit 120 includes multiscale complexity analysis module 150 and PxI audio and/or visual notification module 160. The signal processing unit 120 utilizes the signal, e.g., the iVECG signal, acquired by the acquisition module 140 for the endovascular device positioning and confirmation. Multiscale complexity analysis module 150 may include software programmed for signal data processing. For example, multiscale complexity analysis module 150 may be programmed for processing iVECG signal data acquired from the acquisition module 140 to calculate PxI and/or the distance of the endovascular device from the cavoatrial junction, e.g., using the methods/algorithms discussed in more detail below. Audio and/or visual notification module 160 may include software that signals an associated device (e.g., a monitor, computer, audio device, and/or other display) to provide the user with an audio and/or visual indication/notification of PxI and/or the proximity of the endovascular device to the cavoatrial junction. The audio and/or visual notification may take a variety of forms, including as a graphical or numerical display of PxI, a graphical or numerical display of distance between the endovascular device and the cavoatrial junction, a graphical representation of the endovascular device moving relative to a graphical representation of the heart and/or SVC (e.g., a moving image of a CVC tip may be shown in an image of the SVC as it approaches the cavoatrial junction), a sound (e.g., a beep) that changes frequency as the endovascular device approaches the desired location, display colors may change as the endovascular device progresses (e.g., a red color may be displayed if the tip approaches to closely to the atrium), etc., and/or any combination of these.

Optionally, the signal processing unit 120 may be embedded in the CVC placement unit 110, for example, if the CVC placement unit 110 has a built in digital signal processing unit (DSP), e.g., as in the Sherlock 3CG® Tip Confirmation System. Alternatively, the signal processing unit 120 may utilize a separate DSP connected to CVC placement unit 110. The signal processing unit 120 and/or DSP may be implemented using integrated circuits, microprocessors, field-programmable gate arrays (FPGAs), digital signal controllers, stream processors, software, and/or other components.

Figure 2:
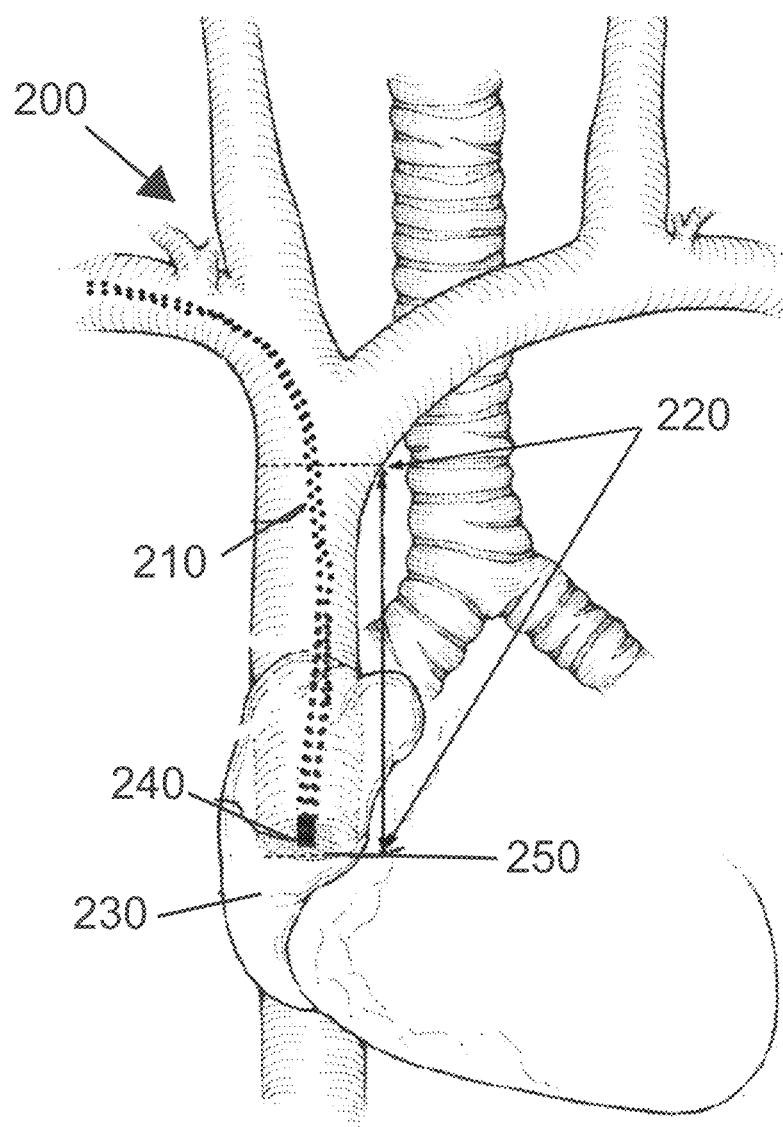
FIG. 2 shows the placement of a CVC in the SVC.

FIG. 2 shows a drawing of a heart 200 and surrounding vasculature. CVC 210 has an iVECG electrode type tip 240, and CVC 210 is shown placed in SVC 220 in an optimal position at the border 250 between the atrium 230 and SVC 220, i.e., the cavoatrial junction.

As shown in FIG. 2, a CVC 210 having an iVECG electrode tip 240 may be inserted into the vasculature or a blood vessel of a patient. CVC 210 is initially inserted into the patient's vasculature or blood vessel through a skin insertion site, e.g., an incision. Initial insertion may be done using an introducer. CVC 210 generally includes a proximal portion (not shown) that remains exterior to the patient and a distal portion that resides within the patient's vasculature after placement is complete. The catheter proximal portion may include a hub that provides fluid communication between the one or more lumens of the CVC 210 and one or more extension legs extending from the hub.

Figure 3:
FIG. 3 shows a plotted ivECG time series recorded by an ivECG device.

As CVC 210 is inserted and advanced through the vasculature or blood vessel, the iVECG electrode tip 240 may be used to sense an iVECG signal of a patient. Accordingly, the iVECG electrode tip 240 may be part of CVC placement unit 110. It is noted that the CVC placement unit 110 may include and iVECG signal data of a patient may be gathered by many types of electrocardiographic devices, i.e., the ECG device used is not limited to one with one electrode located at the tip of a CVC. Further, the ECG device may include various components/features that work in combination, e.g., iVECG electrode tip 240 may function in combination with other features to detect the iVECG signal. FIG. 3 shows a representative iVECG waveform 300 acquired by an ECG device with a sense electrode located at the tip of the catheter, e.g., similar to CVC 110. FIG. 3 also shows a P wave 302.

The complexity of changes to an ECG signal, e.g., a signal similar to iVECG waveform 300, may be used to calculate the distance from the catheter tip to the cavoatrial junction. The method is based on chaos theory and the concept of self-organized criticality (SOC). Systems at critical transition point between chaos and order are said to be in a state of self-organized criticality. The concept of SOC may be applied in different areas such as biological systems, statistics, nature, and large electronic circuits. Many complex biological systems of interaction elements operate "on the edge of chaos," at a critical transition point between randomness and order. A chaotic system is characterized by 'unpredictability,' which simply means that one cannot predict how a system will behave in the future, on the basis of a series of observations over time. Systems on the edge of chaos are said to be in a state of Self-Organized Criticality (SOC). These systems are on the boundary between stable orderly behavior and unpredictable world of chaos. SOC emerges from studies of complex systems of interactive elements.

Dynamics of action potentials have a complex nature; accordingly, an iVECG signal has a complex nature. This complexity derives from interactions between several physiological variables, ANS and CNS regulation, hemodynamic forces, baroreceptor reflex, and others.

Takens' theorem states that it is possible to reconstruct a high dimensional system by observing a single output variable (F. Takens (1981). "Detecting strange attractors in turbulence." In D. A. Rand and L.-S. Young. Dynamical Systems and Turbulence, Lecture Notes in Mathematics, vol. 898. Springer-Verlag. pp. 366-381).

The methods of this disclosure may utilize iVECG data obtained by an electrocardiographic device (ECG device) as the single output variable of Takens' theorem. iVECG is an output of a complex cardiovascular system which operates in a state of SOC and follows the laws of chaos.

One method for the evaluation of complexity of high-dimensional, SOC systems, includes measuring the complexity of the system by using entropy. However, entropy-based or any other methods of measuring complexity at one scale may provide misleading results while assessing threshold levels of complexity, because data with different properties may produce vastly different results.

The method introduced herein uses, in one embodiment, Multiscale Complexity Analysis (MSCA) of dynamics of iVECG data using a Complementary Probability Cumulative Distribution Function, also called Tail Distribution, adapted for the analysis of dynamics of iVECG data. Tail Distribution is defined by the following equation (where P is the probability that the random variable X takes on a value more than x):

$$\overline{F}(x) = P(X > x)$$

An ECG device outputs the time series of iVECG data as a set of measured voltage amplitudes, $\{v_1, v_2, v_3, \ldots v_i, v_{i+1}, \ldots v_n\}$. iVECG time series is transformed to the time series of differences of successive points $\{d_1, d_2, d_3, \ldots d_i,$ $d_{i+1}, \ldots d_{n-1}\}$ where $d_i$ is the absolute difference, $|v_{i+1}-v_i|$ between successive points $v_{i+1}$ and $v_i$.

$P_i$ is the Probability in percentages that the absolute difference between the measured values of Successive Points is more than x.

$$P_i = P(d_i > x), \text{ where } d_i \text{ is } |v_{i+1}-v_i|$$

$P_i$ value at value x=a is the measurement of complexity at scale a. Plotting $P_i$ values with x varying from 0 to maximum of $d_i$ provides a graph of multiscale complexity of ivECG dynamics. $P_i$ represents the tail distribution.

Figure 4:
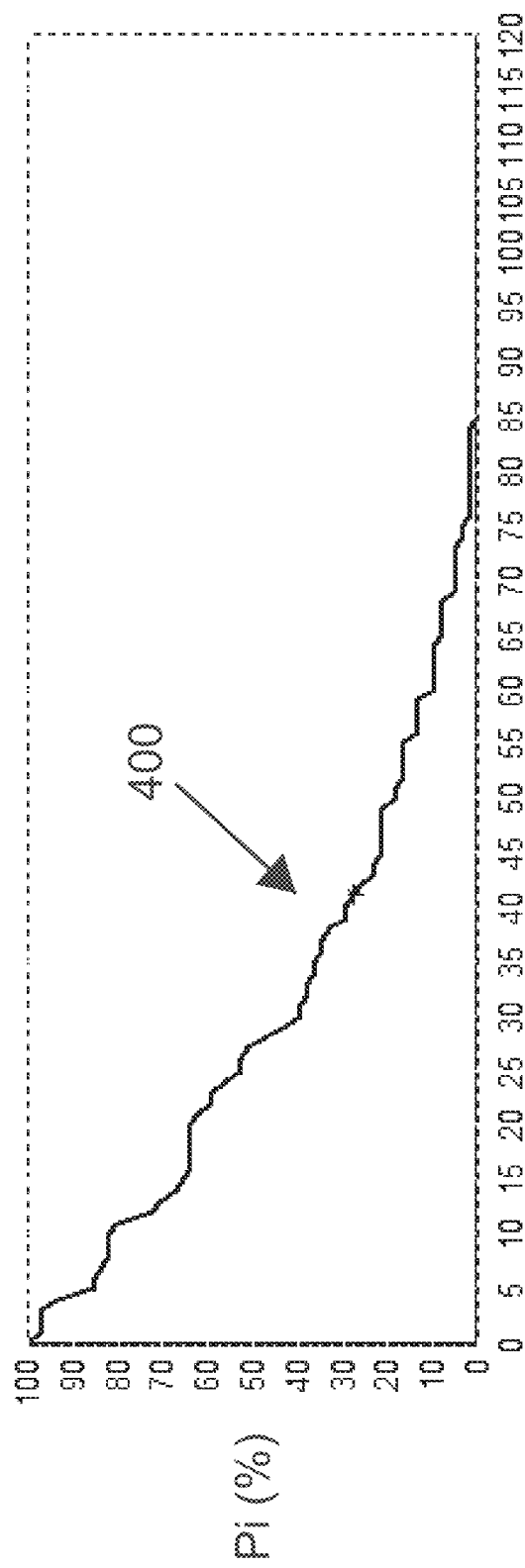
FIG. 4 illustrates a representative tail distribution graph for an ivECG time series.
Figure 5:
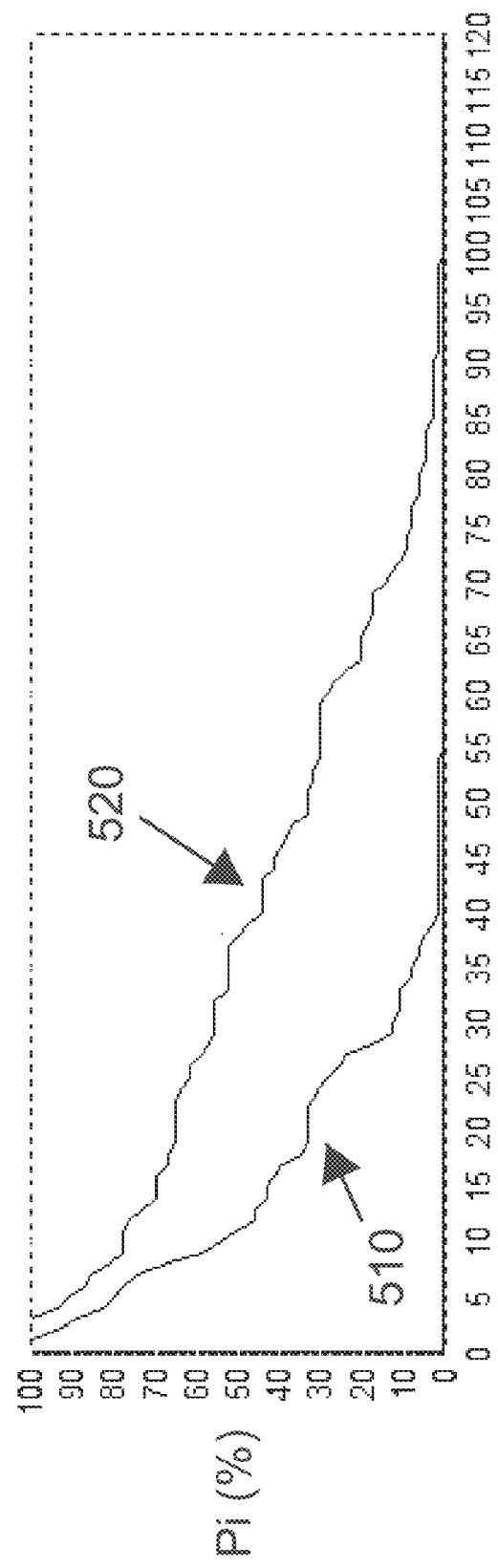
FIG. 5 shows tail distribution graphs of an ivECG time series at the entrance of the SVC and in close proximity to the cavoatrial junction.

FIG. 4 shows a graphical representation of the tail distribution 400 for the ivECG signal/time series 300 in FIG. 3. Whereas, FIG. 5 depicts a tail distribution curve 510 of another ivECG signal as measured at the entrance of the SVC, and a tail distribution curve 520 of ivECG signal as measured in close proximity to the cavoatrial junction. The tail distributions of various ivECG signals, e.g., as shown in FIGS. 3 and 4, may be calculated using the above equations. Referring again to FIG. 1, algorithms may be programmed into multiscale complexity analysis module 150 to perform these functions and calculate tail distributions for signals acquired by acquisition module 840.

Proximity Index (PxI) is calculated as a density of Tail Distribution Function (TDF) which is defined as $$TDF[a \le x \le b] = \int_a^b f(x) \, dx$$

For discrete values (e.g., discrete values of ivECG signal data) the equation becomes as follows (where max is an empirical cut off value representing maximal difference between the largest and smallest two consecutive values of $v_i$ and $v_{i+1}$):

$$TDf[0 \le x \le \max] = \sum_{i=0}^{max} p_i x_i$$

Figure 6:
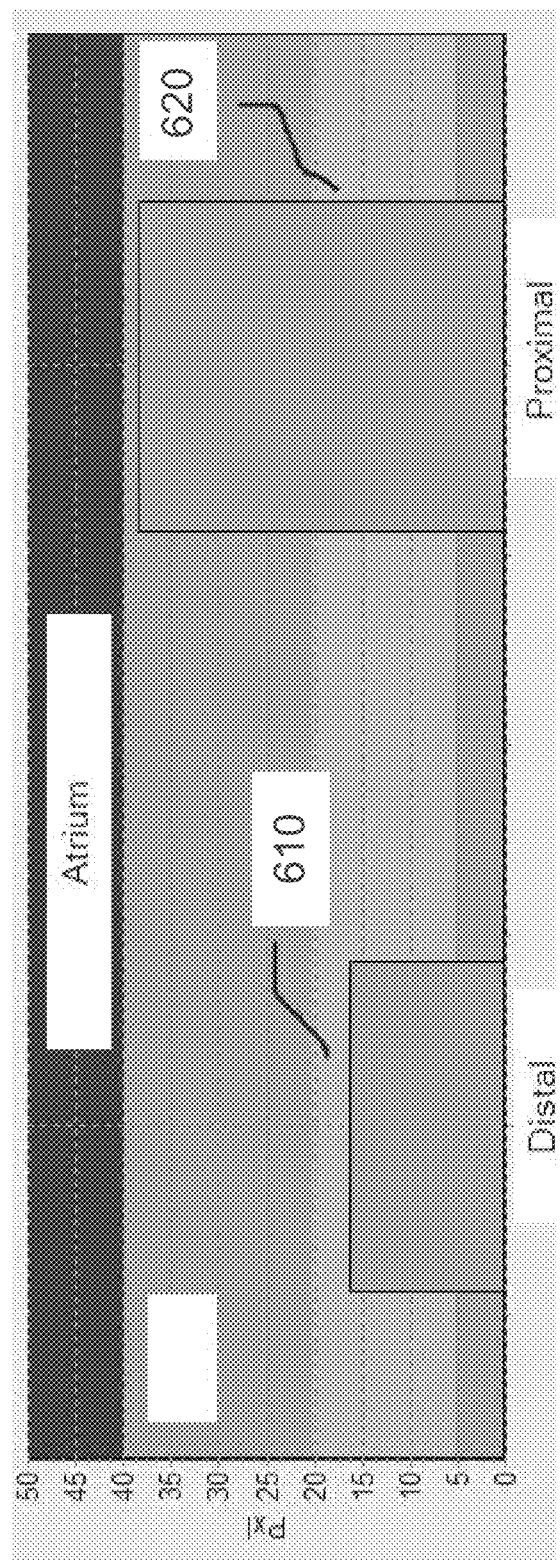
FIG. 6 illustrates the Proximity Index (PxI) or the density of the tail distribution shown in FIG. 5.
Figure 7:
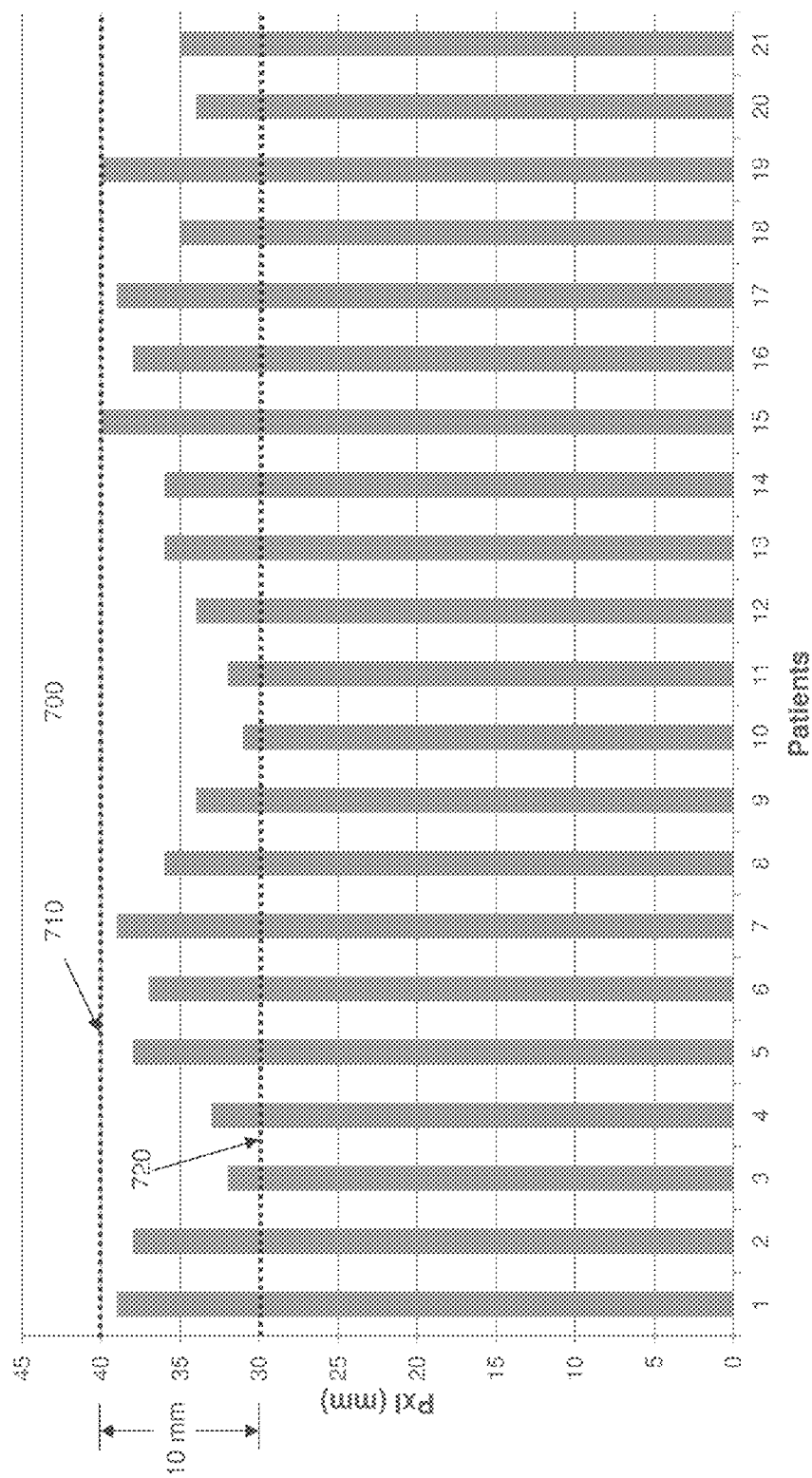
FIG. 7 shows PxI values for a group of 21 patients.

FIG. 6 illustrates graphical representations of PxI values for the ivECG signals used to form the tail distributions of FIG. 5, including PxI value 610 of the ivECG signal measured at the entrance of the SVC, and PxI value 620 of the ivECG signal measured in close proximity to the cavoatrial junction. FIG. 7 shows a graphical representation 700 of actual PxI values for the tip confirmation of 21 patients. All placements of the CVC tip are within 10 mm from the cavoatrial junction as represented by the dotted line 710 at the nominal value 40 of PxI. In other words, the PxI values for each patient are above the proximity threshold shown by dotted line 720. When the PxI values cross the proximity threshold 720 at the nominal value of 30 PxI, this indicates that the tip of the CVC catheter is within the 10 mm of the cavoatrial junction. If the PxI values crossed threshold 710, this would indicate that the tip of the CVC catheter has passed the cavoatrial junction and entered the atrium. Using this method of analysis a clinician does not need to "cross-the-line" or enter the atrium to know when the tip is correctly placed. PxI values of various ivECG signals, e.g., as shown in FIGS. 6 and 7, may be calculated using the above equations. Referring again to FIG. 1, algorithms may be programmed into multiscale complexity analysis module 150 to perform these functions and calculate PxI and correlate PxI to distance between the endovascular device and the cavoatrial junction, e.g., the distance between the tip of a CVC and the cavoatrial junction.

Figure 8:
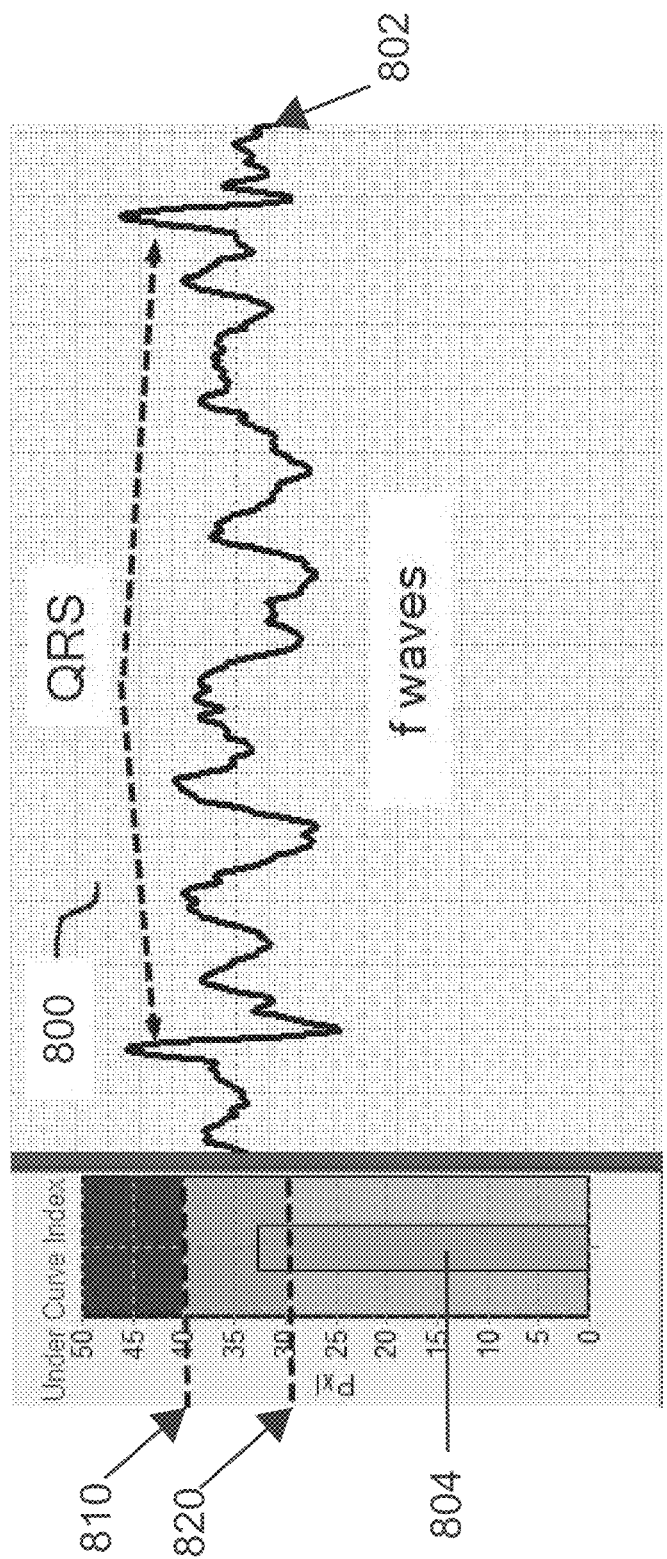
FIG. 8 shows a PxI value for a patient with atrial fibrillation and a corresponding ivECG time series.

FIG. 8 illustrates the CVC tip confirmation 800 for a patient with atrial fibrillation. The ivECG signal data 802 for the patient is shown on the right, and the PxI value 804 calculated from this signal data is shown on the left. A proximity threshold 820 signaling the point at which the tip is within 10 mm of the cavoatrial junction and a threshold 810 signaling the point at which the tip is at the cavoatrial junction are also shown. As shown in the ivECG signal data 802 of FIG. 8, P wave analysis is impossible during atrial fibrillation, e.g., because P waves are absent or distorted. This can be seen by comparing the signal data 802 of FIG. 8 with the signal data 300 and P wave 302 of FIG. 3. Accordingly, methods using assessment of morphological changes of P waves of ivECG are not applicable for patients with atrial fibrillation. In contrast, the above method of placing an endovascular device or assessing location of an endovascular device using multiscale complexity analysis and identifying PxI and comparing it with a proximity threshold is unaffected by atrial fibrillation. Accordingly, the disclosed method allows for accurate placement of the endovascular device even in cases of atrial fibrillation or other distortion of the waveform.

All of the methods disclosed and claimed herein may be made and executed without undue experimentation in light of the present disclosure. While the methods of this invention have been described in terms of particular embodiments, it will be apparent to those skilled in the art that variations may be applied to the methods and in the steps, or in the sequence of steps, of the method described herein without departing from the concept, spirit, and scope of the invention, as defined by the appended claims. It should be especially apparent that the principles of the invention may be applied to selected veins and arteries other than, or in addition to, the SVC to achieve particular results.

Components of the apparatuses, systems, and methods described herein may be implemented in hardware, software, or a combination of both. Where components of the apparatuses, systems and/or methods are implemented in software, the software (e.g., software including the algorithms discussed above) may be stored in an executable format on one or more non-transitory machine-readable mediums. Further, the algorithms and/or steps of the methods described above may be implemented in software as a set of data and instructions. A machine-readable medium includes any mechanism that provides (e.g., stores and/or transports) information in a form readable by a machine (e.g., a computer). For example, a machine-readable medium includes read only memory (ROM); random access memory (RAM); magnetic disk storage media; optical storage media; flash memory devices; DVD's, electrical, optical, acoustical or other form of propagated signals (e.g., carrier waves, infrared signals, digital signals, EPROMs, EEPROMs, FLASH, magnetic or optical cards, or any type of media suitable for storing electronic instructions. The information representing the apparatuses and/or methods stored on the machine-readable medium may be used in the process of creating the apparatuses and/or methods described herein. Hardware used to implement the invention may include integrated circuits, microprocessors, FPGAs, digital signal controllers, stream processors, and/or other components.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A medical system for placement of an endovascular device comprising:
   an electrode usable to acquire intravascular ECG (ivECG) signal data;
   a multiscale complexity analysis module including software, the software comprising instructions to determine at least one proximity index (PxI) value based on the ivECG signal data acquired by the electrode; and
   a device configured to provide one or both of a visual indication and an audio indication of one or both of a PxI and a proximity of the endovascular device to a part of a patient's body, wherein the device is configured to provide a user with one or both of the visual indication and the audio indication of one or both of the PxI and the proximity of the endovascular device to the part of the patient's body based on a comparison of the at least one PxI value with a proximity threshold.

2. The medical system according to claim 1, wherein the endovascular device is a central venous catheter and the part of the patient's body is a cavoatrial junction of the patient's body.

3. A method of positioning an endovascular device in a patient's body, comprising:
   advancing the endovascular device into vasculature of the patient's body with an electrode positioned near a tip of the endovascular device;
   using the electrode to acquire intravascular ECG (ivECG) signal data;
   receiving one or both of an audio output and a visual output indicative of proximity of the endovascular device to a part of the patient's body, wherein the proximity of the endovascular device to the part of the patient's body is determined, at least in part, by comparing at least one proximity index (PxI) parameter, calculated using the ivECG signal data, with a proximity threshold indicating a location of the endovascular device in relation to the part of the patient's body before providing the one or both of the audio output and the visual output.

4. The method according to claim 3, wherein the at least one PxI parameter is calculated from the ivECG signal data using a multiscale complexity analysis module including software programmed for processing the ivECG signal data.

5. The method according to claim 3, wherein the endovascular device is a central venous catheter having a tip and the electrode is attached to the central venous catheter, and wherein advancing the endovascular device into the vasculature includes advancing the central venous catheter into the vasculature.

6. The method according to claim 5, wherein the part of the patient's body is a cavoatrial junction of the patient's body, and wherein the one or both of the audio output and the visual output are indicative of proximity of the tip of the central venous catheter to the cavoatrial junction of the patient's body.

7. The method according to claim 3, wherein the at least one PxI parameter is a density of tail distribution.

8. The method according to claim 7, wherein the tail distribution is a probability that a random variable X takes on a value more than x.

9. The method according to claim 8, wherein the random variable X belongs to a time series of differences of successive points $\{d_1, d_2, d_3, \ldots d_i, d_{i+1}, \ldots d_{n-1}\}$ where $d_i$ is an absolute difference, $|v_{i+1} - v_i|$ between successive points $v_{i+1}$ and $v_i$ of the ivECG signal data.

10. The method according to claim 9 wherein the x is variable from 0 to maximal value $d_i$ from the time series $\{d_1, d_2, d_3, \ldots d_i, d_{i+1}, \ldots d_{n-1}\}$.

11. The method according to claim 3, wherein the one or both of the audio output and the visual output comprises a graphical output shown on a display.

12. A method of positioning an endovascular device in a patient's body, comprising:
    advancing the endovascular device into vasculature of the patient's body with an electrode positioned near a tip of the endovascular device;
    using the electrode to acquire intravascular ECG (ivECG) signal data;
    receiving one or both of an audio output and a visual output indicative of proximity of the endovascular device to a part of the patient's body, wherein the proximity of the endovascular device to the part of the patient's body is determined by at least one proximity index (PxI) parameter calculated using the ivECG signal data, wherein the at least one PxI parameter is a density of tail distribution.

13. The method according to claim 12, wherein the tail distribution is a probability that a random variable X takes on a value more than x.

14. The method according to claim 13, wherein the random variable X belongs to a time series of differences of successive points $\{d_1, d_2, d_3, \ldots d_i, d_{i+1}, \ldots d_{n-1}\}$ where $d_i$ is an absolute difference, $|v_{i+1} - v_i|$ between successive points $v_{i+1}$ and $v_i$ of the ivECG signal data.

15. The method according to claim 14, wherein the x is variable from 0 to maximal value $d_i$ from the time series $\{d_1, d_2, d_3, \ldots d_i, d_{i+1}, \ldots d_{n-1}\}$.

16. The method according to claim 12, wherein the one or both of the audio output and the visual output comprises a graphical output shown on a display.

17. The method according to claim 12, wherein the proximity of the endovascular device to the part of the patient's body is determined, at least in part, by comparing the at least one PxI parameter with a proximity threshold indicating a location of the endovascular device in relation to the part of the patient's body before providing the one or both of the audio output and the visual output.

18. The method according to claim 17, wherein the at least one PxI parameter is calculated from the ivECG signal data using a multiscale complexity analysis module including software programmed for processing the ivECG signal data.

19. The method according to claim 12, wherein the endovascular device is a central venous catheter having a tip and the electrode is attached to the central venous catheter, and wherein advancing the endovascular device into the vasculature includes advancing the central venous catheter into the vasculature.

20. The method according to claim 19, wherein the part of the patient's body is a cavoatrial junction of the patient's body, and wherein the one or both of the audio output and the visual output are indicative of proximity of the tip of the central venous catheter to the cavoatrial junction of the patient's body.

* * * * *